United States Patent [19]

Fletcher et al.

[11] 4,146,500
[45] Mar. 27, 1979

[54] TRIAZOLE COMPOUNDS

[75] Inventors: Ian J. Fletcher, Magden; Guglielmo Kabas, Aesch, both of Switzerland

[73] Assignee: CV I B Ciba-Geigy Corporation, Ardsley, N.Y.

[21] Appl. No.: 633,305

[22] Filed: Nov. 19, 1975

[30] Foreign Application Priority Data

Dec. 6, 1974 [CH] Switzerland ...................... 16251/74

[51] Int. Cl.² .......................................... C07D 239/70
[52] U.S. Cl. .......................... 252/301.21; 252/301.29; 252/301.35; 542/436; 542/445; 8/1 W; 544/254; 544/310
[58] Field of Search ............ 260/240 C, 240 D, 240.9, 260/256.4 F, 251 A; 252/301.21, 301.29, 301.35; 542/436, 445

[56] References Cited

U.S. PATENT DOCUMENTS

| | | | |
|---|---|---|---|
| 2,543,333 | 2/1951 | Parker et al. | 260/240 CA |
| 3,119,820 | 1/1964 | Adams et al. | 260/240 CA |
| 3,272,831 | 9/1966 | Buell et al. | 260/240 CA |
| 3,641,010 | 2/1972 | Schweiss et al. | 260/240 D |
| 3,819,645 | 6/1974 | Kirchmayr | 260/308 B |
| 3,830,804 | 8/1974 | Barbee et al. | 260/240 D |

OTHER PUBLICATIONS

Jezo et al., Chem. Zvesti 6 (1952), p. 357.

*Primary Examiner*—Arthur P. Demers
*Attorney, Agent, or Firm*—Prabodh I. Almaula

[57] ABSTRACT

New triazole compounds of formula

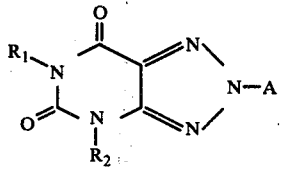

wherein $R_1$ represents alkyl of 1 to 6 carbon atoms, $R_2$ represents alkyl of 1 to 6 carbon atoms or phenyl which is unsubstituted or substituted by halogen, alkyl of 1 to 4 carbon atoms or alkoxy of 1 to 4 carbon atoms, and A represents a radical of certain compounds selected from stylbenes, 2-phenyl-4-styryl-v-triazoles, 3-phenyl-coumarines, 2-phenyl-benzoxazoles, 2-phenyl-benzimidazoles, 2-phenyl-v-triazolo[d]pyrimidine-5,7-diones and 2-biphenyl-v-triazolo[d]pyrimidine-5,7-diones, a process for their preparation as well as a process for optically brightening organic material on using said compounds are disclosed.

12 Claims, No Drawings

TRIAZOLE COMPOUNDS

The present invention relates to new triazole derivatives, a process for their manufacture and also to their use as fluorescent brighteners for organic material of high molecular weight.

According to the present invention there are provided triazole compounds of formula

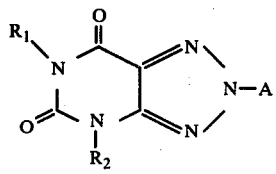
(1)

wherein $R_1$ represents alkyl of 1 to 6 carbon atoms, $R_2$ represents alkyl of 1 to 6 carbon atoms, unsubstituted phenyl or phenyl which is substituted by halogen, alkyl of 1 to 4 carbon atoms or alkoxy of 1 to 4 carbon atoms, and A represents a radical of formula

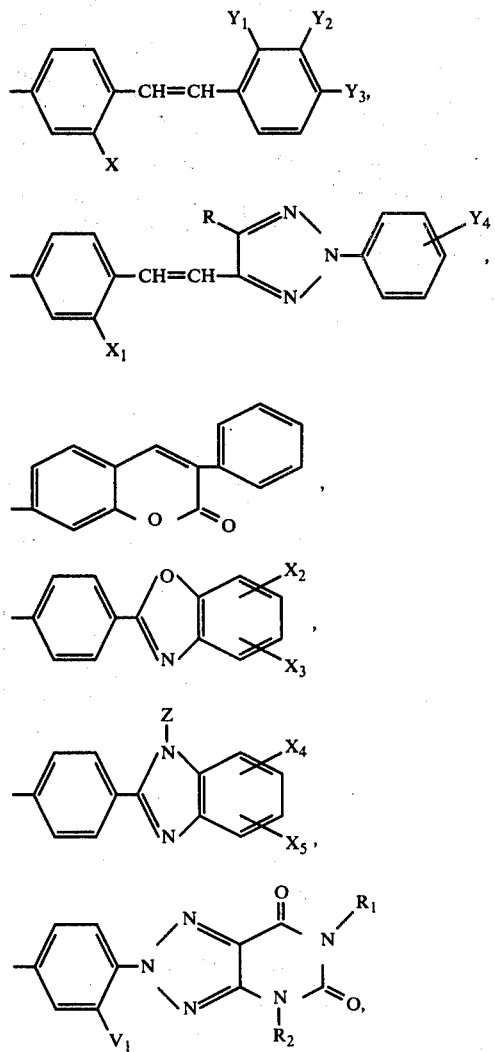

or

-continued

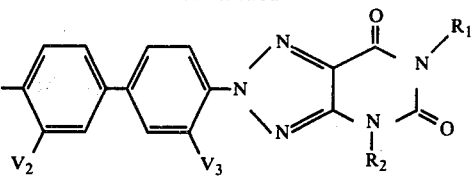

wherein X represents hydrogen, cyano, sulpho or alkylsulphonyl of 1 to 4 carbon atoms, $Y_1$ represents hydrogen, chlorine or alkoxy of 1 to 4 carbon atoms, $Y_2$ represents hydrogen, chlorine, alkoxy of 1 to 4 carbon atoms or together with $Y_3$ represents methylenedioxy, $Y_3$ represents hydrogen, chlorine, alkyl of 1 to 6 carbon atoms, alkoxy of 1 to 4 carbon atoms, phenyl, carbalkoxy of 2 to 5 carbon atoms or together with $Y_2$ represents methylenedioxy, $X_1$ represents hydrogen, cyano, alkylsulphonyl of 1 to 4 carbon atoms, sulpho, sulphamoyl which is unsubstituted or mono- or disubstituted by alkyl of 1 to 4 carbon atoms, or morpholinosulphonyl, R represents hydrogen, methyl or phenyl, $Y_4$ represents hydrogen, alkyl of 1 to 4 carbon atoms, alkylsulphonyl of 1 to 4 carbon atoms, chlorine, or alkoxy in meta-position of 1 to 4 carbon atoms, $X_2$ represents hydrogen, alkyl of 1 to 4 carbon atoms, chlorine, or alkoxy in 5- or 6-position of 1 to 4 carbon atoms, phenyl, alkylsulphonyl of 1 to 4 carbon atoms or carbalkoxy of 2 to 5 carbon atoms, $X_3$ represents hydrogen or methyl, $X_4$ represents hydrogen, alkyl of 1 to 4 carbon atoms, chlorine, or alkylsulphonyl in 5- or 6-position of 1 to 4 carbon atoms, $X_5$ represents hydrogen or methyl, Z represents hydrogen, alkyl of 1 to 4 carbon atoms, phenyl or benzyl, $V_1$ represents hydrogen, chlorine, or alkoxy of 1 to 4 carbon atoms, and each of $V_2$ and $V_3$ independently represents hydrogen or sulpho.

The term "sulpho" is to be understood as meaning the radical -$SO_3M$, wherein M represents hydrogen or a salt-forming cation. Possible salt-forming cations are in general those of alkaline earth metals, for example calcium, barium, magnesium, and also especially of alkali metals, for example sodium or potassium, and also ammonium which is substituted by alkyl or hydroxyalkyl of 1 to 4 carbons or is unsubstituted. M preferably represents hydrogen, potassium and sodium.

Particularly interesting compounds are those wherein $R_1$ and $R_2$ are identical and preferably represent alkyl of 1 to 6, in particular 1 to 4, carbon atoms.

Particularly important types of compound within the scope of formula (1) are:

A. Compounds of Formula

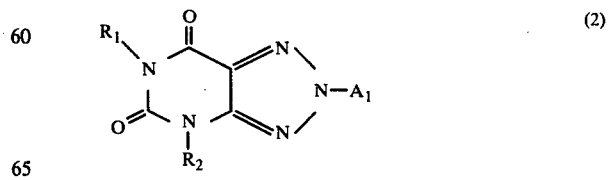
(2)

wherein $R_1$ and $R_2$ are as defined hereinbefore and $A_1$ represents a radical of formula

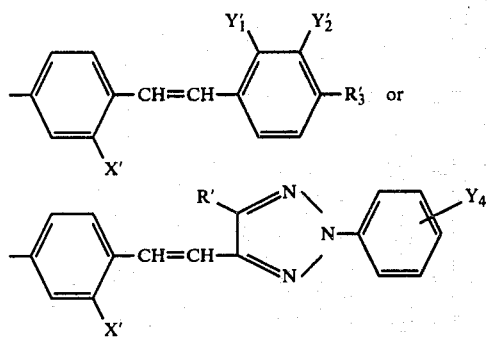

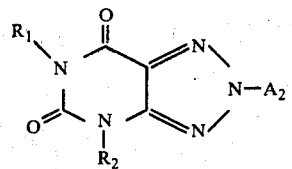

wherein $R_1$ and $R_2$ are as defined hereinbefore and $A_2$ represents a radical of formula

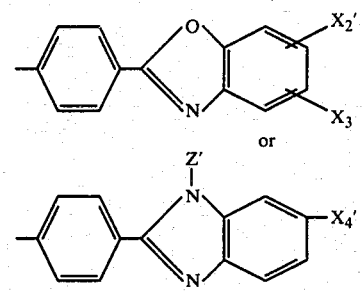

wherein X' represents hydrogen, cyano, sulpho or alkylsulphonyl of 1 to 4 carbon atoms, $Y_1'$ represents hydrogen or chlorine, $Y_2'$ represents hydrogen, chlorine, or alkoxy of 1 to 4 carbon atoms, $Y_3'$ represents hydrogen, chlorine, alkyl of 1 to 4 carbon atoms, phenyl, or carbalkoxy of 2 to 5 carbon atoms, R' represents hydrogen or methyl, and $Y_4$ represents hydrogen, alkyl of 1 to 4 carbon atoms, sulpho, alkylsulphonyl of 1 to 4 carbon atoms, chlorine, or alkoxy in meta-position of 1 to 4 carbon atoms.

wherein $X_2'$ represents hydrogen, alkyl of 1 to 4 carbon atoms, alkoxy of 1 to 4 carbon atoms, phenyl, carbalkoxy of 1 to 5 carbon atoms or alkylsulphonyl of 1 to 4 carbon atoms, $X_3$ represents hydrogen or methyl, Z' represents hydrogen or methyl, and $X_4'$ represents hydrogen, alkyl of 1 to 4 carbon atoms, alkylsulphonyl of 1 to 4 carbon atoms, or chlorine.

B. Compounds of Formula

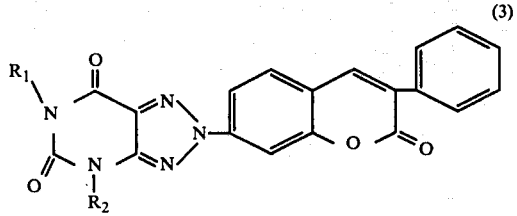

(3)

D. Compounds of Formula

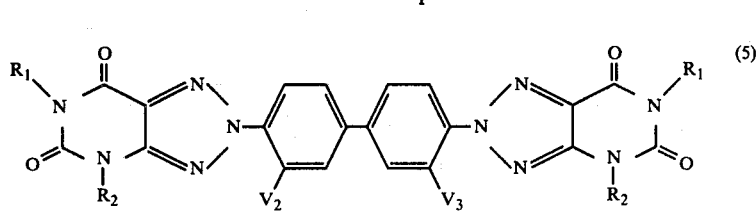

(5)

wherein $R_1$ and $R_2$ are as defined hereinbefore.

wherein $R_1$ and $R_2$ are as defined hereinbefore and each of $V_2$ and $V_3$ independently represents hydrogen or sulpho.

The preferred compound of formula (3) is that of formula

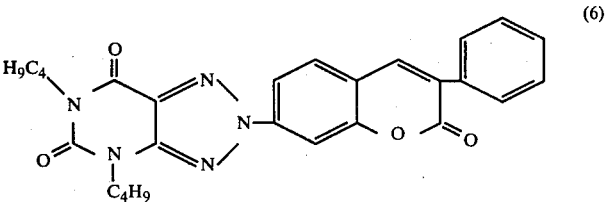

(6)

Particularly interesting compounds within the scope of formula (2) are those of formulae

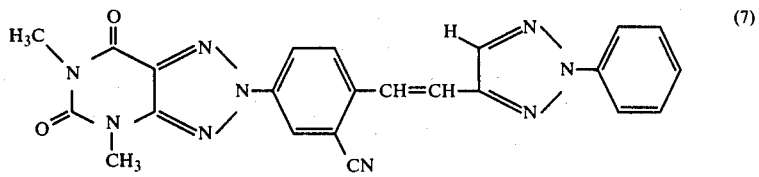

(7)

and

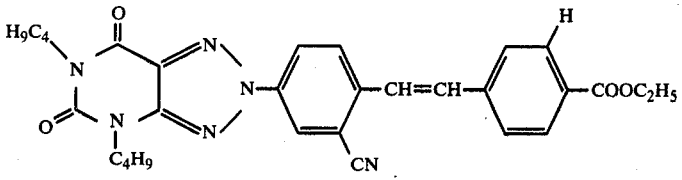

(8)

The compounds of formulae (1) to (8) can be obtained analogously to known methods, for example by coupling an amine of formula

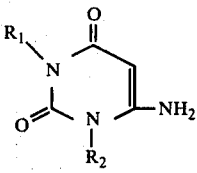

(9)

with a diazonium salt of formula

(10)

and then converting the resultant o-amino compound of formula

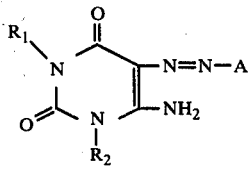

(11)

by cyclisation into a triazole of formula (1) by treatment with an oxidant (cf. J. Jezo and Z. Vozicky, Chem. Zvesti, 6, 357 (1952)).

The oxydative cyclisation can be accomplished by the action of the most different kinds of oxidant, it being advisable to carry out the process in oxidation-resistant solvents. In acid, for example acetic acid, solution, bichromate or hydrogen peroxide are useful oxidants. In basic solvents, for example pyridine or pyridine/water mixtures, a suitable oxidant is e.g. potassium ferricyanide. The customary and therefore preferred process consists in the oxidation with copper (II) sulphate in pyridine/water. Stoichiometric amounts of copper need not be used, because the monovalent copper that is formed during the reaction can be converted continually into the divalent form by bubbling in air or oxygen. It is also advantageous to carry out the oxidation with copper (II) salts, for example copper (II) sulphate or copper (II) chloride, in methanol or methanol/water in the presence of ammonium or amine salts. In this manner it is possible to manufacture all of the above described compounds.

The compounds of formula (4) can also be obtained by converting a carboxylic acid of the general formula

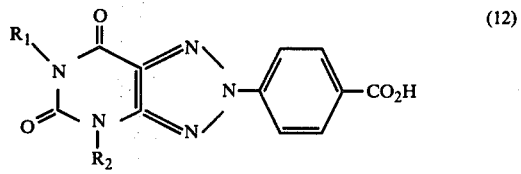

(12)

into a benzoxazole or benzimidazole derivative by known methods. The manufacture of such carboxylic acid intermediates can also be effected in the manner described above.

The compounds of the present invention defined hereinbefore have a more or less pronounced fluorescence when in solution or suspension. They can be used for optically brightening synthetic man-made, regenerated man-made or natural organic materials of the most widely different kind or substances which contain such organic materials.

Without any restriction being implied by the following classification, examples of organic materials are:

I. Synthetic organic materials of high molecular weight:

(a) polymerisation products based on organic compounds containing at least one polymerisable carbon-carbon double bond, that is to say their homopolymers or copolymers as well as their aftertreatment products, for example, crosslinking, grafting or degradation products, polymer blends, or products obtained by modification of reactive groups, for example polymers based on α, β-unsaturated carboxylic acids or derivatives of such carboxylic acids, especially on acrylic compounds, for example acrylic esters, acrylic acid, acrylonitrile, acrylic amides and their derivatives or their methacryl analogues), on olefin hydrocarbons (for example ethylene, propylene, styrenes or dienes and also ABS polymers), and polymers based on vinyl and vinylidene compounds (for example vinyl chloride, vinyl alcohol and vinylidene chloride);

(b) polymerisation products which can be obtained by ring opening, for example, polyamides of the polycaprolactam type, and also polymers which are obtained both by polyaddition and by polycondensation, for example polyethers or polyacetals, (c) polycondensation products or precondensates based on bifunctional or polyfunctional compounds with condensable groups, their homocondensation and co-condensation products, and aftertreatment products, for example polyesters, especially saturated (for example ethylene glycol terephthalic acid polyester) or unsaturated (for example maleic acid-dialcohol polycondensates as well as their crosslinking products with copolymerisable vinyl monomers), unbranched and branched (also including those based on polyhydric alcohols, for example alkyd resins) polyesters, polyamides (for example hexamethylenediamine adipate), maleic resins, melamine resins, their precondensates and analogues, polycarbonates and silicones;

(d) polyaddition products, such as polyurethanes (crosslinked and non-crosslinked) and epoxide resins.

II. Regenerated man-made organic materials, for example, cellulose esters of varying degrees of esterification (so-called 2½ acetate or triacetate) or cellulose ethers, regenerated cellulose (viscose or cuprammonium cellulose), or their aftertreatment products, and casein plastics.

III. Natural organic materials of animal or vegetable origin, for example based on cellulose or proteins, such as cotton, wool, linen, silk, varnish gums, starch and casein.

The organic materials to be optically brightened can be in the most diverse states of processing (raw materials, semi-finished goods or finished goods). On the other hand, they can be in the form of structures of the most diverse shapes, for example predominantly three-dimensional structures such as sheets, profiles, injection mouldings, various machined articles, chips, granules or foams, and also predominantly two-dimensional structures, such as films, foils, lacquers, coatings and impregnations, or predominantly one-dimensional bodies, such as filaments, fibres, flocks and wires. The said materials can, on the other hand, also be in an unshaped state, in the most diverse homogeneous or inhomogeneous forms of division, as for example, in the form of powders, solutions, emulsions, dispersions, latices, pastes or waxes.

Fibre materials can, for example, be in the form of endless filaments (stretched or unstretched), staple fibres, flocks, hanks, textile filament yarns, threads, non-wovens, felts, waddings, flocked structures or woven textile or bonded textile fabrics, knitted fabrics and papers, cardboards or paper pulps.

The compounds to be used according to the invention are of importance, inter alia, for the treatment of organic textile materials, especially woven textile fabrics. If fibres which can be in the form of staple fibres or endless filaments or in the form of hanks, woven fabrics, knitted fabrics, fleeces, flocked substrates or bonded fabrics, are to be optically brightened according to the invention, this is advantageously effected in an aqueous medium, wherein the compounds in question are present in a finely divided form (suspensions, so-called microdispersions, or optionally solutions). If desired, dispersing agents, stabilisers, wetting agents and further assistants can be added during the treatment.

Depending on the type of brightener compound used, it can be advantageous to carry out the treatment in a neutral or alkaline or acid bath. The treatment is usually carried out at temperatures of 20° to 140° C., for example at the boiling point of the bath or near it (above 90° C.). Solutions or emulsions in organic solvents can also be used for the finishing according to the invention of textile substrates, as is practised in the dyeing industry in so-called solvent dyeing (pad-heat fixing application, or exhaustion dyeing processes in dyeing machines).

The fluorescent brighteners of the present invention can further be added to, or incorporated in, the materials before or during their shaping. Thus they can for example be added to the compression moulding composition or injection moulding composition during the manufacture of films, sheets (for example working into polyvinyl chloride in a single roller mill at elevated temperature) or mouldings.

If the fashioning of man-made synthetic or regenerated man-made organic materials is effected by spinning processes or from spinning solutions/melts, the fluorescent brightheners can be applied by the following processes:

addition to the starting substances (for example monomers) or intermediates (for example precondensates or prepolymers), that is to say before or during the polymerisation, polycondensation or polyaddition, sprinkling in powder form on polymer chips or granules for spinning solutions/melts, both dyeing of polymer chips or granules for spinning solutions/melts, metered addition to spinning melts or spinning solutions, and application to the spun tow before stretching.

The fluorescent brighteners according to the present invention can, for example, also be employed in the following use forms:

(a) in mixtures with dyestuffs (shading) or pigments (coloured pigments or especially, for example, white pigments), or as an additive to dye baths, printing pastes, discharge pastes or reserve pastes, or for the aftertreatment of dyeings, prints or discharge prints;

(b) in mixtures with carriers, wetting agents, plasticisers, swelling agents, anti-oxidants, ultraviolet absorbers, heat stabilisers and chemical bleaching agents (chlorite bleach or bleaching bath additives);

(c) in admixture with crosslinking agents or finishing agents (for example starch or synthetic finishes), and in combination with the most diverse textile finishing processes, especially synthetic resin finishes (for example creaseproof finishes such as wash-and-wear, permanent-press or non-iron), as well as flameproof finishes, soft handle finishes, anti-soiling finishes or anti-static finishes, or antimicrobial finishes;

(d) incorporation of the fluorescent brighteners into polymeric carriers (polymerisation, polycondensation or polyaddition products, in a dissolved or dispersed form, for use, for example, in coating agents, impregnating agents or binders (solutions, dispersions and emulsions) for textiles, non-wovens, papers and leather;

(e) as additives to master batches;

(f) as additives to the most diverse industrial products in order to render these more marketable (for example improving the appearance of soaps, detergents, pigments);

(g) in combination with other optically brightening substances;

(h) in spinning bath preparations, that is to say as additives to spinning baths which are used for improving the slip for the further processing of synthetic fibres, or from a special bath before the stretching of the fibre;

(i) as scintillators for various purposes of a photographic nature, for example, for electrophotographic reproduction, for the optical brightening of photographic layers, optionally in combination with white pigments, for example $TiO_2$.

Depending on the substitution, the compounds of the present invention are also suitable as laser dyes for emission in the range of short-wave visible light.

If the brightening process is combined with textile treatment or finishing methods, the combined treatment can in many cases advantageously be carried out with the aid of appropriate stable preparations which contain the fluorescent brightener compounds in such a concentration that the desired brightening effect is achieved.

In certain cases, the fluorescent brighteners are made fully effective by an after-treatment. This can be, for example, a chemical treatment (for example acid treatment), a thermal treatment (for example heat) or a combined chemical/thermal treatment. Thus, for example, the appropriate procedure to follow in brightening a number of fibre substrates, for example polyester fibres, with the fluorescent brighteners according to the invention, is to impregnate these fibres with the aqueous dispersions (or optionally also solutions) of the brighteners at temperatures below 75° C., for example at room temperature, and to subject them to a dry heat treatment at temperatures above 100° C., it being generally advisable additionally to dry the fibre material beforehand at a moderately elevated temperature, for example at not less than 60° C. and up to about 130° C. The heat treatment in the dry state is then advantageously carried out at temperature between 120° and 225° C., for example by heating in a drying chamber, by ironing within the specified temperature range or by treatment with dry, superheated steam. The drying and dry heat treatment can also be carried out in immediate succession or be combined in a single process step.

The amount of fluorescent brightener manufactured according to the invention to be used, referred to the weight of the material to be brightened, can vary within wide limits. A marked and lasting effect can be obtained even with very insignificant amounts, in certain cases 0.0005 percent by weight. But it is also possible to use amounts of up to app. 0.8 percent by weight and, on occasion, up to app. 2 percent by weight. For most practical purposes, it is preferable to use amounts between 0.005 and 0.5 percent by weight.

The fluorescent brighteners of this invention are also particularly suitable for use as additives to wash liquors or heavy duty and domestic detergents, to which they can be added in various ways. They are appropriately added to wash liquors in the form of their solutions in water or organic solvents or, in a finely divided form, as aqueous dispersions. They are advantageously added to domestic or heavy duty detergents in any stage of the manufacturing process of the detergents, for example to the slurry before the washing powder is atomised, or during the preparation of liquid detergent combinations. They can be added either in the form of a solution or dispersion in water or other solvents or, without assistants, as a dry brightening powder. For example, the brightening agents can be mixed, kneaded or ground with the active detergents and, in this form, admixed with the finished powder. However, they can also be sprayed in a dissolved or pre-dispersed form on the finished detergent.

Suitable detergents are the known mixtures of active detergents, for example soap in the form of chips and powders, synthetics, soluble salts of sulphonic acid half esters of higher fatty alcohols, arylsulphonic acids with higher and/or multiple alkyl substituents, sulphocarboxylic acid esters of medium to higher alcohols, fatty acid acylaminoalkyl- or acylaminoaryl-glycerol sulphonates and phosphoric acid esters of fatty alcohols. Suitable builders which can be used are, for example, alkali metal polyphosphates and polymetaphosphates, alkali metal pyrophosphates, alkali metal salts of carboxymethylcellulose and other soil redeposition inhibitors, and also alkali metal silicates, alkali metal carbonates, alkali metal borates, alkali metal perborates, nitrilotriacetic acid, ethylenediaminotetraacetic acid, and foam stabilisers such as alkanolamides of higher fatty acids. The detergents can further contain for example: antistatic agents, fat restorative skin protection agents, such as lanolin, enzymes, anti-microbial agents, perfumes and dyestuffs.

The new fluorescent brighteners have the particular advantage that they are also active in the presence of active chlorine donors, for example, hypochlorite, and can be used without significant loss of effect in wash liquors containing non-ionic washing agents, for example alkylphenolpolyglycol ethers.

The compounds according to the invention are added in amounts of 0.005 to 1% or more, based on the weight of the liquid or pulverulent finished detergent. Washing liquors which contain the indicated amounts of the fluorescent brighteners claimed impart a brilliant appearance in daylight when used to wash textiles made from cellulose fibres, polyamide fibres, cellulose fibres with a high quality finish, polyester fibres or wool.

The washing treatment is carried out as follows, for example:

The textiles are treated for 1 to 30 minutes at 20° to 100° C. in a wash liquor which contains 1 to 10 g/kg of a built-up composite detergent and 0.05 to 1%, based on the weight of the detergent, of the claimed brightening agents. The liquor ratio can be 1:3 to 1:50. After they have been washed, the textiles are rinsed and dried in the usual manner. The wash liquor can contain 0.2 g/l of active chlorine (for example as hypochlorite) or 0.1 to 2 g/l of sodium perborate as a bleaching additive.

In the following examples, parts and percentages are always by weight, unless otherwise stated. Unless indicated to the contrary, melting points and boiling points are uncorrected.

EXAMPLE 1

A mixture of 23.7 g of 7-amino-3-phenylcumarin, 100 ml of water, 50 ml of concentrated hydrochloric acid, 35 g of quartz sand and a small amount of octanol is stirred overnight and the yellow suspension is freed from sand. The suspension is cooled to 10° C. in a beaker with stirring and diazotised at this temperature with 7.25 g of sodium nitrile dissolved in 15 ml of water. The diazotisation is terminated after a further 2 hours at 10° C.–15° C. and a light yellow suspension is obtained. The 15.5 g of 6-amino-1,3-dimethyluracil are suspended in 400 ml of pyridine. This suspension is cooled to 0° C. and treated at 0°–5° C. with the diazonium salt suspension in the course of 30 minutes. An orange suspension is at once obtained. The coupling is terminated after 2 hours at 10°–15° C. and the product is filtered off with suction, washed with water and dried at 100° C. in vacuo. This crude product is then suspended in 350 ml of pyridine, and the suspension is heated to 60° C. and treated at this temperature with a solution of 62.4 g of copper sulphate pentahydrate in 250 ml of water in the course of 30 minutes. The mixture is subsequently stirred for 4 hours at 90° C.–95° C. and poured into 3 litres of water. The product is filtered off with suction, washed with 5% hydrochloric acid and water and dried in vacuo at 100° C. Yield of crude product: 39.1 g (=98% of theory). Two recrystallisations from o-dichlorobenzene and treatment with fuller's earth yield the product in the form of yellow crystals of formula (13). The yield amounts to 57% of theory and the melting point is 313°–314° C.

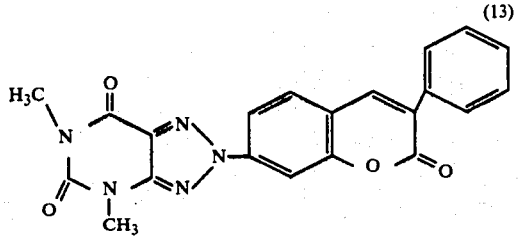
(13)

Starting from different 6-amino-1,3-disubstituted uracils and amines it is possible to obtain in analogous manner the compounds of the general formula (14) listed in Table I.

Table I (14)

| Formula | U | $U_1$ | D | Melting point uncorr. in °C |
|---|---|---|---|---|
| (15) | $nC_4H_9$ | $nC_4H_9$ | (phenyl-coumarin group) | 129–131 |
| (16) | $CH_3$ | $C_6H_5$ | (phenyl-coumarin group) | 329–330 |
| (17) | $CH_3$ | $CH_3$ | –CH=CH–$C_6H_5$ with CN | 324–325 |
| (18) | $CH_3$ | $CH_3$ | –CH=CH–$C_6H_4$–$CO_2C_2H_5$ with CN | 293–294 |
| (19) | $CH_3$ | $C_6H_5$ | –CH=CH–$C_6H_4$–$CO_2C_2H_5$ with CN | 306–308 |
| (20) | $nC_4H_9$ | $nC_4H_9$ | –CH=CH–$C_6H_4$–$CO_2C_2H_5$ with CN | 202–203 |
| (21) | $CH_3$ | $CH_3$ | –CH=CH–$C_6H_5$ with $SO_3Na$ | >350 |
| (22) | $CH_3$ | $CH_3$ | –CH=CH–$C_6H_4$–$OCH_3$ with CN | 327–328 |
| (23) | $CH_3$ | $CH_3$ | –CH=CH–$C_6H_4$–$OCH_3$ with CN | 303–304 |

Table I-continued

Structure (14):
U-N, with fused pyrimidine-triazine system bearing =O groups, N-D substituent, and N-U₁.

| Formula | U | U₁ | D | Melting point uncorr. in °C |
|---|---|---|---|---|
| (24) | CH₃ | CH₃ | -C₆H₃(CN)-CH=CH-C₆H₄-C₆H₅ (biphenyl) | 322–323 |
| (25) | CH₃ | CH₃ | -C₆H₃(CN)-CH=CH-CH=N-N(phenyl) | 309–310 |
| (26) | CH₃ | CH₃ | -C₆H₃(CN)-CH=CH-C₆H₃(OCH₂O) (methylenedioxyphenyl) | 327–329 |
| (27) | CH₃ | CH₃ | -C₆H₄-N=N-triazine-pyrimidinedione(N,N-dimethyl) | >350 |
| (28) | CH₃ | CH₃ | -C₆H₃(SO₃Na)-CH=CH-C₆H₄-C₆H₅ | >350 |
| (29) | CH₃ | CH₃ | -C₆H₃(SO₃Na)-C₆H₃(SO₃Na)-N-N=... triazine-pyrimidinedione(N,N-dimethyl) | >350 |

EXAMPLE 2

30.1 g of 2-(p-carboxyphenyl)-5,7-diketo-4,6-dimethyl-v-triazole-(4,5-d)-pyrimidine are suspended in 400 ml of thionyl chloride and the suspension is heated to reflux temperature, with good stirring, in the course of 1½ hours. After a further 2 hours a clear, dark yellow solution is obtained. This solution is cooled to 20° C. and excess thionyl chloride is evaporated off. The residue is treated with toluene and the product precipitates in the form of yellow crystals, which are filtered off with suction, washed with toluene and petroleum ether and dried in vacuo at 100° C. Yield: 25.7 g of the carboxylic acid chloride (=81% of theory) which melts at 222°–224° C. A mixture of 18.5 g of the above carboxylic acid chloride and 5.45 g of o-aminophenol is refluxed for 1 hour in 200 ml of o-dichlorobenzene. After the mixture has cooled to 20° C., the precipitated product is filtered off with suction, washed with methanol and dried. Yield: 15.6 g (80% of theory) of the crude amide which melts above 250° C. 15.6 g of this carboxy amide and 1.5 g of boric anhydride are refluxed for 30 minutes in 250 ml of dibutyl phthalate. After the mixture has cooled to 20° C., the precipitated product is filtered off with suction. Repeated recrystallisation from o-dichlorobenzene with fuller's earth yields the benzoxazole in the form of pale yellow crystals of formula (30).

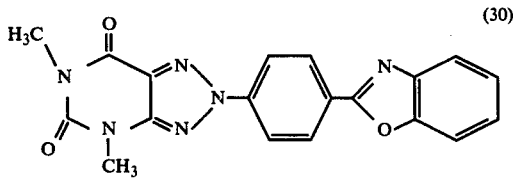

(30)

The yield is 19.6 g (=67% of theory) and the melting point is 302°–303° C. The compound of formula (31) which melts at 314°–316° C. is obtained in analogous manner by using 2-amino-5-phenylphenol in the second step instead of o-aminophenol.

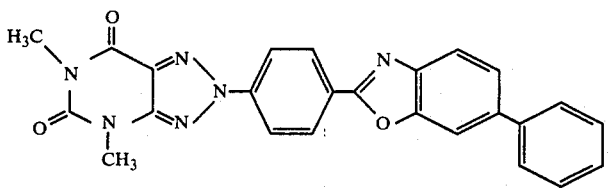

(31)

EXAMPLE 3

5.65 g of o-nitroaniline are dissolved in 80 ml of pyridine and to the resultant dark red solution are added at room temperature and by small amounts in the course of 30 minutes 12.5 g of the carboxylic acid chloride obtained in Example 2. The mixture warms of its own accord to 30° C. and the acylation product separates as a yellow crystalline substance. After termination of the addition, the batch is stirred for 1 hour at room temperature and then for 1 hour at 80°-85° C. After cooling to 20° C., the product is filtered off with suction, washed with alcohol and dried. Yield: 13.5 g (82% of theory) of a product which melts at 266°-267° C.

13.5 g of this product are suspended in 350 ml of ethylene glycol monomethyl ether and heated to 80°-90° C. At this temperature, a solution of 34.2 g of tin (II) chloride dihydrate in 65 ml of concentrated hydrochloric acid is added dropwise in the course of 25 minutes. With gentle warming, a turbid, fluorescent solution is obtained. After stirring for 3 hours at 105°-110° C., the pale yellow suspension is cooled to 50° C. and poured into 1500 ml of 10% sodium hydroxde solution. The precipitated yellow crystals are collected by suction filtration and washed neutral with water. Recrystallisation from dimethyl formamide/water and treatment with animal charcoal yields 3.7 g (=31% of theory) of a pale yellow product of formula (32) which melts at 350° C.

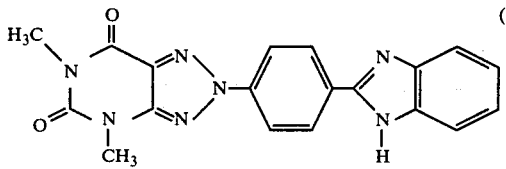

(32)

EXAMPLE 4

To 100 ml of water is added 0.06 g of Tinegal NA ® (=alkylpolyglycol ether). A solution is a fluorescent brightener of formula (13) is prepared by dissolving 1 g in 1000 ml of dimethyl formamide. Then 3 ml of this stock solution are added to the first solution above. This aqueous solution or dispersion containing the brightener is heated to 60° C. and then 3 g of heavy nylon fabric are put into it. The temperature rises to 92°-95° C. in the course of 10-15 minutes and kept thereat for 30 minutes. The fabric is then rinsed for 2 minutes in running cold water and subsequently dried for 20 minutes at 60° C. The treated fabric has a distinct white effect. Similar effects are also obtained with the other compounds of Examples 1 to 3.

EXAMPLE 5

To 100 ml of water is added 0.2 g of Irgacarrier TC ® (=trichlorobenzene). A solution of the fluorescent brightener of formula (13) is prepared by dissolving 1 g in 1000 ml of dimethyl formamide. Then 1.5 ml of this stock solution is added to the first solution above. This aqueous solution containing the brightener is heated to 60° C. and then 3 g of heavy polyester fabric is put into it. The temperature is raised to 95°-98° C. in the course of 10-15 minutes and held thereat for 1 hour. The fabric is then rinsed in running cold water and subsequently dried for 20 minutes at 60° C. The treated fabric has a distinct white effect. Similar effects are also obtained with the other compounds of Examples 1 to 3.

EXAMPLE 6

A solution of the fluorescent brightener of formula (13) is prepared by dissolving 1 g in 1000 ml of dimethyl formamide. A polyester fabric is padded with this solution (20° C.) and squeezed out to a pick-up of 50-60% (roller pressure 30 kg/cm², speed 3 m/min.). The fabric is then dried for 20 minutes at 60° C. The dry fabric is subsequently fixed for 30 seconds at 200° C. The treated fabric has a distinct white effect.

EXAMPLE 7

A mixture of 67 parts of polyvinyl chloride powder, 33 parts of dioctyl phthalate, 2 parts of di-n-butyl-dilauryl-dioxystannate, 0.3 part of sodium pentaoctyl tripolyphosphate and 0.05 part of the fluorescent brightener of formula (13) is gelatinised on a mixer roll for 15 minutes at 160° C. and subsequently drawn out to sheets. The resultant polyvinyl chloride sheet has a strong fluorescence in daylight and a brilliant white appearance.

EXAMPLE 8

1000 parts of polyester granulate of polyterephthalic acid and ethylene glycol are intimately mixed with 0.25 part of the fluorescent brightener of formula (13) and then, under nitrogen, spun to filaments through a spinneret in known manner from an extruder at a temperature of 265° to 285° C. The resultant polyester filaments have a brilliant white appearance. Similar effects are also obtained with the other compounds of Examples 1 to 3.

We claim:

1. Triazole compounds of formula

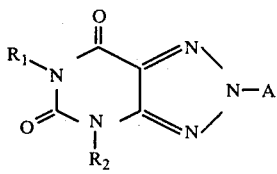

wherein $R_1$ represents alkyl of 1 to 6 carbon atoms, $R_2$ represents alkyl of 1 to 6 carbon atoms or phenyl which is unsubstituted or substituted by halogen, alkyl of 1 to 4 carbon atoms or alkoxy of 1 to 4 carbon atoms, and A represents a radical of formula

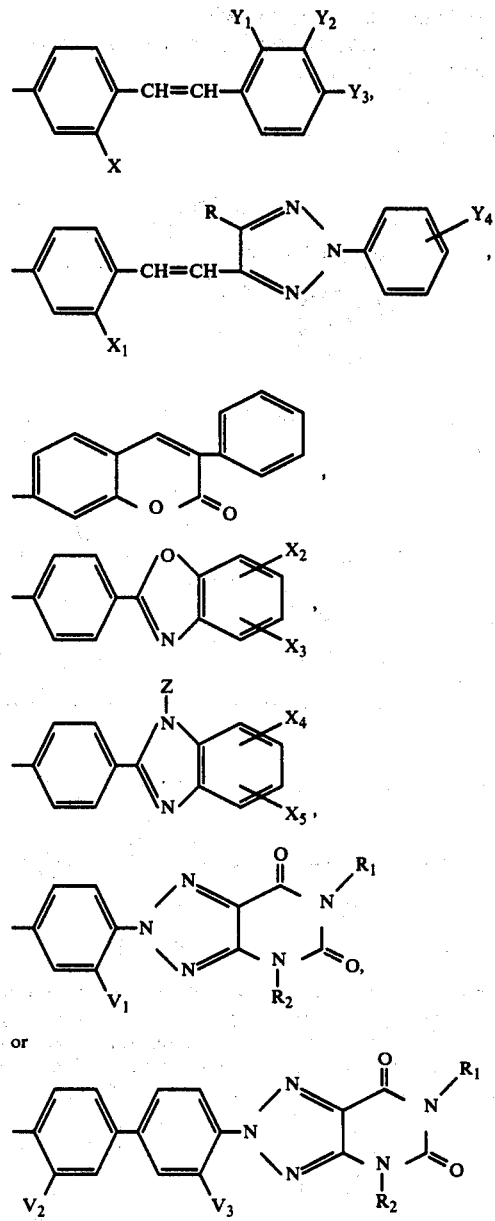

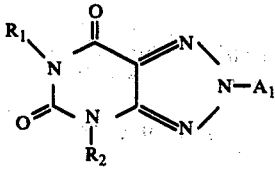

wherein X represents hydrogen, cyano, sulpho or alkylsulphonyl of 1 to 4 carbon atoms Y₁ represents hydrogen, chlorine or alkoxy of 1 to 4 carbon atoms, Y₂ represents hydrogen, chlorine, alkoxy of 1 to 4 carbon atoms or together with Y₃ represents methylenedioxy Y₃ represents hydrogen, chlorine, alkyl of 1 to 6 carbon atoms, alkoxy of 1 to 4 carbon atoms, phenyl, carbalkoxy of 2 to 5 carbon atoms, or together with Y₂ represents methylenedioxy, X₁ represents hydrogen, cyano, alkylsulphonyl of 1 to 4 carbon atoms, sulpho, sulphamoyl which is unsubstituted or mono- or disubstituted by alkyl of 1 to 4 carbon atoms, or morpholinosulphonyl, R represents hydrogen, methyl or phenyl, Y₄ represents hydrogen, alkyl of 1 to 4 carbon atoms, alkylsulphonyl of 1 to 4 carbon atoms, chlorine, or alkoxy in meta-position of 1 to 4 carbon atoms, X₂ represents hydrogen, alkyl of 1 to 4 carbon atoms, chlorine, or alkoxy in 5- or 6-position of 1 to 4 carbon atoms, phenyl, alkylsulphonyl of 1 to 4 carbon atoms or carbalkoxy of 2 to 5 carbon atoms, X₃ represents hydrogen or methyl, X₄ represents hydrogen, alkyl of 1 to 4 carbon atoms, chlorine, or alkylsulphonyl in 5- or 6-position of 1 to 4 carbon atoms, X₅ represents hydrogen or methyl, Z represents hydrogen, alkyl of 1 to 4 carbon atoms, phenyl or benzyl, V₁ represents hydrogen, chlorine, or alkoxy of 1 to 4 carbon atoms, and each of V₂ and V₃ independently represents hydrogen or sulpho.

2. Triazole compounds according to claim 1 of formula

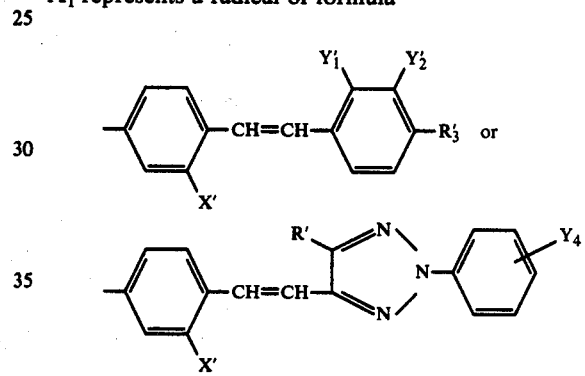

wherein R₁ represents alkyl of 1 to 6 carbon atoms, R₂ represents alkyl of 1 to 6 carbon atoms or phenyl which is unsubstituted or substituted by halogen, alkyl of 1 to 4 carbon atoms or alkoxy of 1 to 4 carbon atoms, and A₁ represents a radical of formula

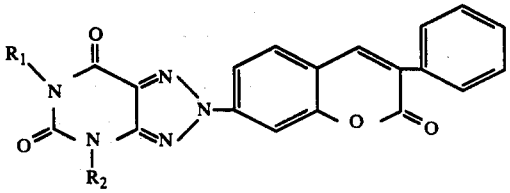

wherein X' represents hydrogen, cyano, sulpho or alkylsulphonyl of 1 to 4 carbon atoms, Y₁' represents hydrogen or chlorine, Y₂' represents hydrogen, chlorine or alkoxy of 1 to 4 carbon atoms, Y₃' represents hydrogen, chlorine alkyl of 1 to 4 carbon atoms, phenyl, or carbalkoxy of 2 to 5 carbon atoms, R' represents hydrogen or methyl, and Y₄ represents hydrogen, alkyl of 1 to 4 carbon atoms, sulpho, alkylsulphonyl of 1 to 4 carbon atoms, chlorine, or alkoxy in meta-position of 1 to 4 carbon atoms.

3. Triazole compounds according to claim 1 of formula wherein R₁ represents alkyl of 1 to 6 carbon atoms and R₂ represents alkyl of 1 to 6 carbon atoms or phenyl which is unsubstituted or substituted by halogen, alkyl of 1 to 4 carbon atoms or alkoxy of 1 to 4 carbon atoms.

4. Triazole compounds according to claim 1 of formula

wherein $R_1$ represents alkyl of 1 to 6 carbon atoms, $R_2$ represents alkyl of 1 to 6 carbon atoms or phenyl which is unsubstituted or substituted by halogen, alkyl of 1 to 4 carbon atoms or alkoxy of 1 to 4 carbon atoms, and $A_2$ represents a radical of formula

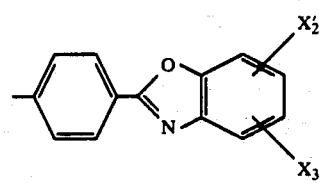

or

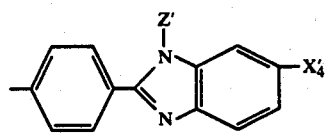

wherein $X_2'$ represents hydrogen, alkyl of 1 to 4 carbon atoms, alkoxy of 1 to 4 carbon atoms, phenyl, carbalkoxy of 2 to 5 carbon atoms or alkylsulphonyl of 1 to 4 carbon atoms, $X_3$ represents hydrogen or methyl, $Z'$ represents hydrogen or methyl, and $X_4'$ represents hydrogen, alkyl of 1 to 4 carbon atoms, alkylsulphonyl of 1 to 4 carbon atoms or chlorine.

5. Triazole compounds according to claim 1 of formula

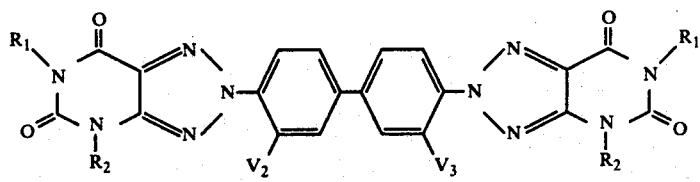

wherein $R_1$ represents alkyl of 1 to 6 carbon atoms, $R_2$ represents alkyl of 1 to 6 carbon atoms or phenyl which is unsubstituted or substituted by halogen or alkyl of 1 to 4 carbon atoms, and each of $V_2$ and $V_3$ independently represents hydrogen or sulpho.

6. A triazole compound according to claim 1 of formula

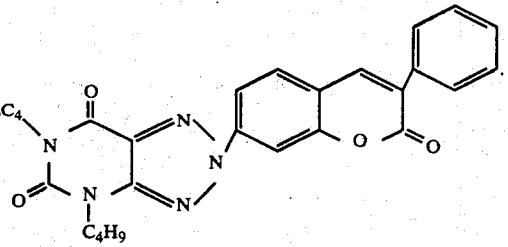

7. A triazole compound according to claim 1 of formula

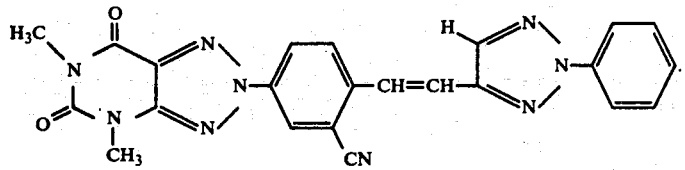

8. A triazole compound according to claim 1 of formula

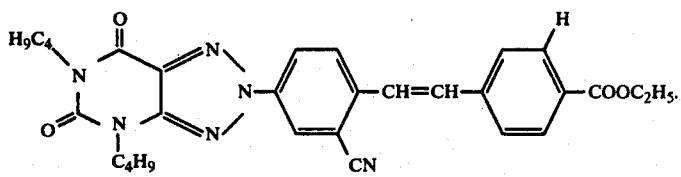

9. In a process for optically brightening a high molecular weight polyamide, polyester or polyvinyl chloride material, the improvement which comprises incorporating in said material, or applying to the surface thereof, a compound of the formula

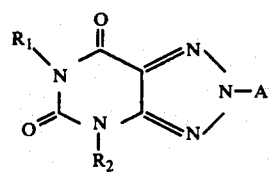

wherein $R_1$ represents alkyl of 1 to 6 carbon atoms, $R_2$ represents alkyl of 1 to 6 carbon atoms or phenyl which is unsubstituted or substituted by halogen, alkyl of 1 to 4 carbon atoms or alkoxy of 1 to 4 carbon atoms, and A represents a radical of formula

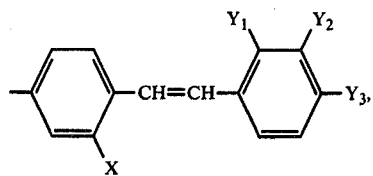

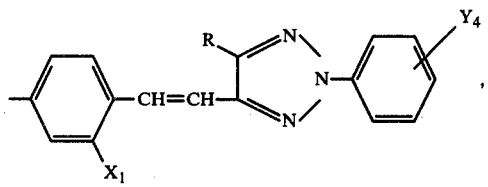

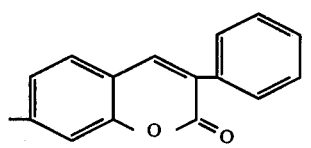

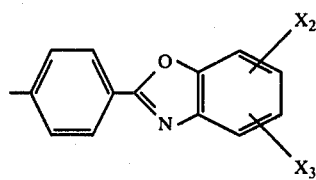

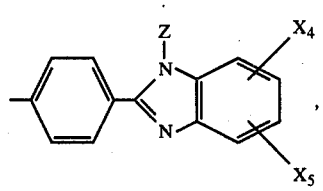

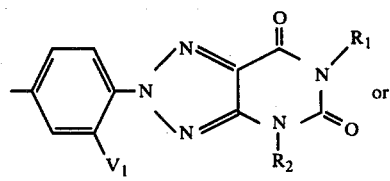

or

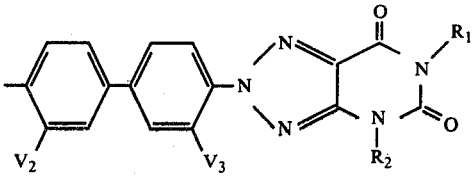

wherein X represents hydrogen, cyano, sulpho or alkylsulphonyl of 1 to 4 carbon atoms $Y_1$ represents hydrogen, chlorine or alkoxy of 1 to 4 carbon atoms, $Y_2$ represents hydrogen, chlorine, alkoxy of 1 to 4 carbon atoms or together with $Y_3$ represents methylenedioxy $Y_3$ represents hydrogen, chlorine, alkyl of 1 to 6 carbon atoms, alkoxy of 1 to 4 carbon atoms, phenyl, carbalkoxy of 2 to 5 carbon atoms, or together with $Y_2$ represents methylenedioxy, $X_1$ represents hydrogen, cyano, alkylsulphonyl of 1 to 4 carbon atoms, sulpho, sulphamoyl which is unsubstituted or mono- or disubstituted by alkyl of 1 to 4 carbon atoms, or morpholinosulphonyl, R represents hydrogen, methyl or phenyl, $Y_4$ represents hydrogen, alkyl of 1 to 4 carbon atoms, alkylsulphonyl of 1 to 4 carbon atoms, chlorine, or alkoxy in meta-position of 1 to 4 carbon atoms, $X_2$ represents hydrogen, alkyl of 1 to 4 carbon atoms, chlorine, or alkoxy in 5- or 6-position of 1 to 4 carbon atoms, phenyl, alkylsulphonyl of 1 to 4 carbon atoms or carbalkoxy of 2 to 5 carbon atoms, $X_3$ represents hydrogen or methyl, $X_4$ represents hydrogen, alkyl of 1 to 4 carbon atoms, chlorine, or alkylsulphonyl in 5- or 6-position of 1 to 4 carbon atoms, $X_5$ represents hydrogen or methyl, Z represents hydrogen, alkyl of 1 to 4 carbon atoms, phenyl or benzyl, $V_1$ represents hydrogen, chlorine, or alkoxy of 1 to 4 carbon atoms, and each of $V_2$ and $V_3$ independently represents hydrogen or sulpho.

10. A process according to claim 9, wherein 0.0005 to 2% by weight of the compound is incorporated in, or applied to the surface of, the material.

11. A process according to claim 9, wherein the compound is applied to the surface of the material by the exhaustion or pad-heat method.

12. A process according to claim 9, wherein the compound is incorporated in polyester spinning solutions or melts.

* * * * *